United States Patent [19]

Farrell et al.

[11] 4,447,883

[45] May 8, 1984

[54] COINCIDENCE-ERROR CORRECTING APPARATUS AND METHOD

[75] Inventors: Gregory A. Farrell, Teaneck, N.J.; Edward A. Epstein, Putnam Valley, N.Y.

[73] Assignee: Technicon Instruments Corporation, Tarrytown, N.Y.

[21] Appl. No.: 266,879

[22] Filed: May 26, 1981

[51] Int. Cl.³ .............................................. G01N 27/00
[52] U.S. Cl. ...................................... 364/555; 377/11; 377/50; 324/71.4
[58] Field of Search .................... 364/555, 571; 377/6, 377/10, 11, 12, 50; 324/71.1, 71.4

[56] References Cited
U.S. PATENT DOCUMENTS

| 3,502,974 | 3/1970 | Coulter et al. | 324/71.7 |
|---|---|---|---|
| 3,626,164 | 12/1971 | Pontigny | 364/555 |
| 3,740,143 | 6/1973 | Groner et al. | 356/39 |
| 3,864,551 | 2/1975 | Oefinger | 377/50 |
| 3,938,038 | 2/1976 | Campbell | 377/50 |
| 3,940,691 | 2/1976 | Hogg | 377/50 |
| 3,944,791 | 3/1976 | Baxter, Jr. | 377/50 |
| 3,987,391 | 10/1976 | Hogg | 377/50 |
| 4,009,443 | 2/1977 | Coulter et al. | 377/50 |
| 4,042,808 | 8/1977 | Hennessy et al. | 377/50 |
| 4,251,768 | 2/1981 | Angel et al. | 377/10 |
| 4,314,346 | 2/1982 | Feier et al. | 364/555 |

Primary Examiner—Gary Chin
Attorney, Agent, or Firm—S. P. Tedesco

[57] ABSTRACT

New and improved method and apparatus for the correction of coincident errors attendant the automated detection and counting of mixed particles having detectable characteristics of different levels in particle counting applications wherein the detection of "dominant" particles under coincident particle conditions, renders undetectable the "dominated" particles, with resulting inaccuracy in the "dominated" particle count. Such inaccuracy is corrected by modifying the "dominated" particle count in accordance with the time duration of the signals which are generated attendant the detection of the "dominated" particles.

9 Claims, 4 Drawing Figures

4,447,883

COINCIDENCE-ERROR CORRECTING APPARATUS AND METHOD

BACKGROUND OF THE INVENTION

1. Field of the Invention

This invention relates to new and improved method and apparatus for the accurate correction of coincidence errors attendant to the automated detection and counting of mixed particles having detectable characteristics of different levels, wherein the detectable characteristics of certain particles (hereinafter referred to as the "dominant" particles), under coincident particle conditions, render undetectable the other of the particles (hereinafter referred to as the "dominated" particles), resulting in an inaccurate count of the dominated particles.

2. Description of the Prior Art

Although prior art methods and apparatus are known for the correction of coincidence errors attendant the automated counting of mixed dominant and dominated particles, none are known which accomplish this function with a truly high degree of accuracy. More specifically, these prior art methods and apparatus are generally limited in operation to a known, standard correction formula to correct for both dominant particle-dominant particle coincidence and dominated particle-dominated particle coincidence. While such formula improves the accuracy of both the dominant and dominated particle counts, it nonetheless totally ignores dominant particle-dominated particle coincidence errors and, hence, a truly accurate correction of the dominated particle count is not achieved.

OBJECTS OF THE INVENTION

An object of this invention is to provide new and improved method and apparatus for the highly accurate correction of coincidence errors attendant the counting of mixed dominant and dominated particles, where the detectable characteristics of the dominant particles, under coincident conditions, render undetectable the dominated particles.

Another object of this invention is the provision of method and apparatus applicable to the detecting and counting of particles having a wide range of detectable characteristics.

A further object of this invention is the provision of method and apparatus which are of relatively simple configuration and operation and which require only the use of readily available, state-of-the-art components.

DESCRIPTION OF THE DRAWINGS

The above and other objects and advantages of our invention are believed made clear by the following detailed description thereof, taken in conjunction with the accompanying drawings wherein.

DETAILED DESCRIPTION OF THE INVENTION

Figure 1:
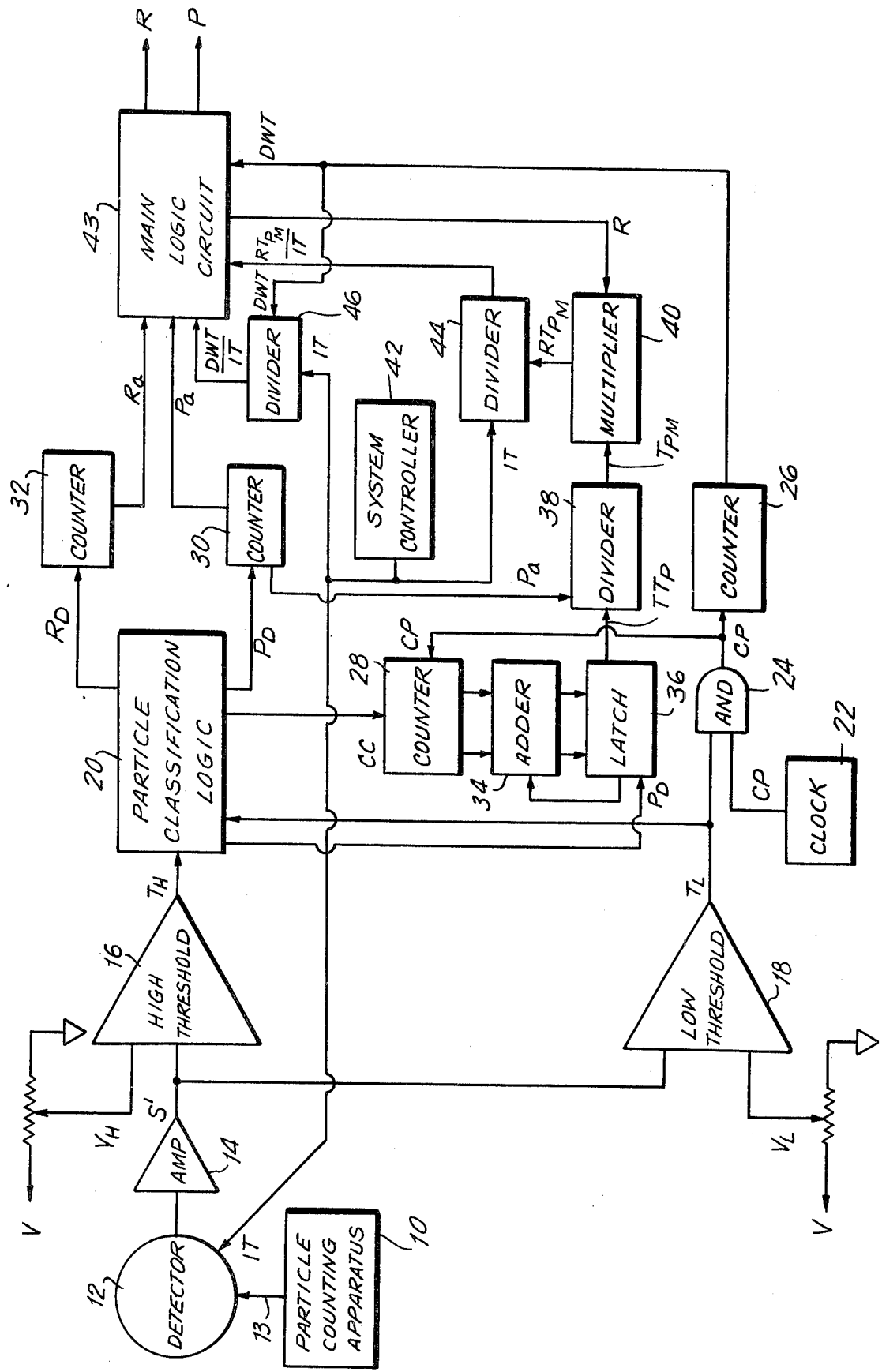
FIG. 1 illustrates a particle counting circuit comprising coincidence errors correction circuitry configured and operable in accordance with the teachings of our invention.

FIG. 1 illustrates a representative application of the present invention to the automated detection and counting of the mixed red blood cells and platelets of a series of blood samples which are passed, for example, through a conventional sheath-stream flow cell of the type described in U.S. Pat. No. 3,661,460 assigned to a common assignee. In such application, the red blood cells, because of their greater size, would constitute the "dominant" particles and the platelets would constitute the "dominated" particles. In a representative blood sample, the red cells normally have approximately eight times the volume and twenty times the frequency, or population, of the platelets.

In FIG. 1, the particle counting apparatus, which would include, inter alia, a sheath-stream flow cell, is indicated at 10 and a particle detector at 12. The output of detector 12 is connected to the input of an amplifier 14, whose output is multiplied by the respective inputs of high and low threshold circuits indicated at 16 and 18. The particle counting circuit further includes particle classification logic circuit 20; a clock pulse source 22; an AND gate 24; and counters 26, 28, 30 and 32. In addition, the particle counting circuit includes an adder 34; a latch 36; a divider circuit 38; and a multiplier circuit 40; also, a system controller 42 which turns the detector 12 on for interrogation time IT while sample is present in counting apparatus 10, and divider circuits 44 and 46. A main logic circuit 43 is responsive to the foregoing components to provide outputs, as indicated, which indicate the coincidence-corrected red blood cell count R and the coincidence-corrected platelet count P.

Figure 2A:
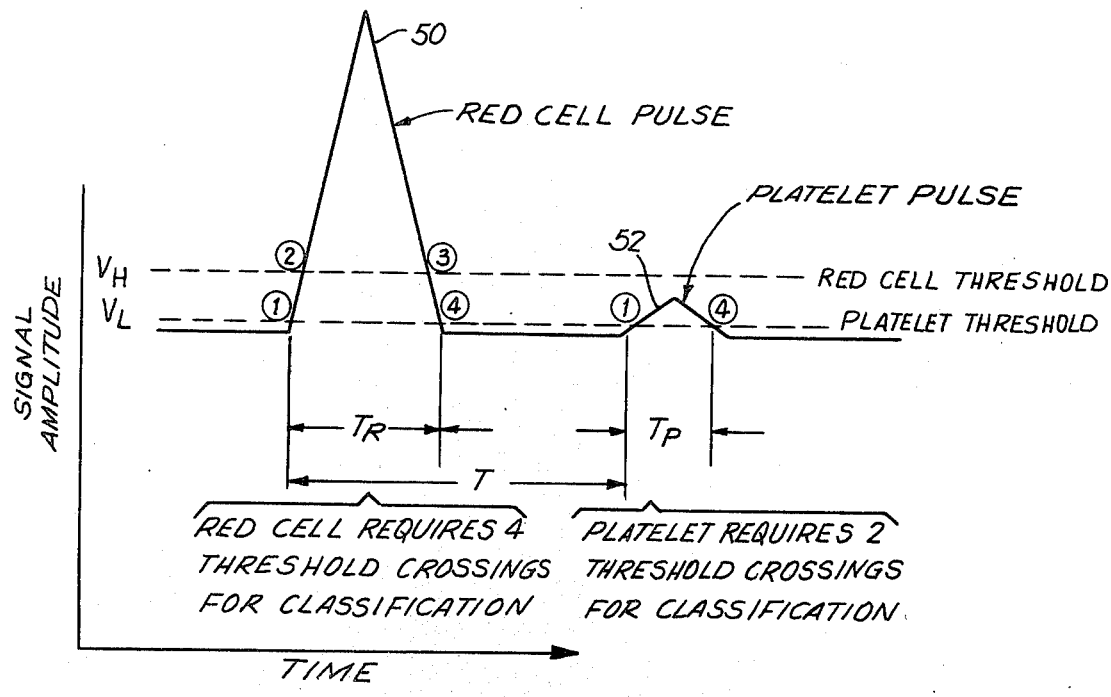
FIGS. 2A and 2B illustrate waveforms useful in understanding the operation of the counting circuit of FIG. 1.
Figure 2B:
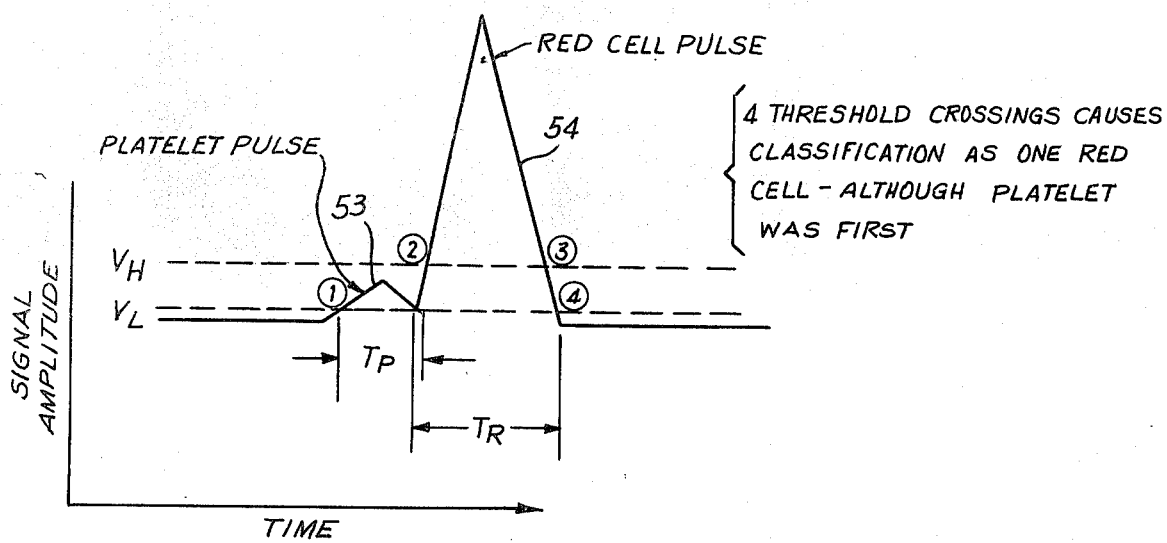

In operation, and referring now to FIGS. 2A and 2B, as a red cell or platelet pass through the non-illustrated sheath-stream flow cell in the particle counting apparatus 10, the forward scattering of the interrogating illumination, as indicated by arrow 13, is detected by detector 12, which generates an output signal in response thereto. FIG. 2A illustrates the output signal generated when a red blood cell passes through the flow cell and is followed, at a finite time interval $T > T_R$ by a platelet. This results in the generation by detector 12 of the red cell pulse 50 and a platelet pulse 52 of pulse widths $T_R$ and $T_P$, respectively. Pulse 50 is substantially greater, as shown, in both duration and amplitude than is pulse 52, due to the substantial disparity in size between the red blood cell and platelet.

High threshold and low threshold levels detection $V_H$ and $V_L$ are indicated by the dashed lines in FIGS. 2A and 2B. Under the conditions of FIG. 2A, there is no coincidence error, since the pulses 50 and 52 are separated in time by interval $T > T_R$. Thus red cell pulse 50 will make four crossings, as indicated at points 1, 2, 3 and 4, of the low and high threshold detection levels $V_L$ and $V_H$ and be detected and counted as a red blood cell. Also, the platelet pulse 52 will make two crossings, only, as indicated at points 1 and 4, of the low threshold level $V_L$ and be counted as a platelet.

FIG. 2B illustrates the condition in which a platelet has not been completely interrogated by particle counting apparatus before the arrival thereat of a red blood cell. Hence, there is a coincidence of pulses 53 and 54, as shown. More specifically, it will be seen that before the platelet pulse 53 has made the requisite second crossing of the low threshold detection level $V_L$ for detection and counting as a platelet, the appearance of a red blood cell pulse 54 results in a coincidence situation, whereby the platelet and the red blood cell would be counted as a single red blood cell, with an attendant inaccuracy in the overall platelet count. In like manner, and although not illustrated, if the platelet were to trail slightly behind but nonetheless is partially overlapped by the red cell, or be totally overlapped by the red blood cell in flowing through the sheath stream flow cell, platelet pulse 53 would fail to make the requisite two crossings of the low threshold level $V_L$ and the output of amplifier 14, in response to the red blood cell would exceed and high threshold level detection level $V_H$, with the resultant loss of a platelet count and the counting only of a red blood cell.

In addition to the red blood cell-platelet, or dominant-dominated particle, coincidence errors, it will be understood that red cell-red cell, i.e., dominant particle-dominant particle, and platelet-platelet, i.e., dominated particle-dominated particle, coincidence error can and do occur.

In such event, the first particle will be detected and counted and the second particle lost. In a dominant particle-dominated particle coincidence situation, the dominant particle is always detected and counted, while the dominated particle is lost, regardless of which is first.

The coincidence correction methods at the prior art correct for coincidence errors in which the later-appearing coincident particle(s) is lost, but not for the loss of a first-appearing dominated particle. The prior art corrects for coincidence errors in accordance with the known standard equations 1 and 2:

$$R = \frac{R_a}{1 - \left(\frac{DWT}{IT}\right)} \qquad 1$$

$$P = \frac{P_a}{1 - \left(\frac{DWT}{IT}\right)} \qquad 2$$

wherein R is the corrected red blood cell count; $R_a$ is the uncorrected red blood cell count; DWT is the total time during which the signal pulses are above the low threshold detection level $V_L$; IT is the total interrogation time during which the detector is "on"; P is the presumably corrected platelet count; and $P_a$ is the uncorrected platelet count.

As a result of the above, and although each of the red blood cell and platelet counts are corrected for particle coincidence, no correction is made in the prior art for red blood cell-platelet coincidence errors, as depicted and/or described hereinabove with respect to FIG. 2B. Thus, the prior art does not provide an accurate platelet, or dominated particle, count P. In the prior art, such platelet count P will, of necessity, be lower than true. Our invention appreciates that the percent error of red blood cell-platelet coincidence is significantly greater, e.g., between half again and double, than the frequency of red blood cell-red blood cell coincidence errors because of the attendant detection error associated with this type of coincidence. Hence, it will be evident that the failure to correct the platelet count P for red blood cell-platelet coincident errors is of particularly disadvantageous consequence with regard to the validity of the corrected platelet count P.

By way of clear distinction, it has been determined in accordance with the teachings of our invention that the apparent platelet, or dominated, particle count $P_a$ can be accurately corrected for red blood cell-platelet coincidence by compensating such count by the mean pulse duration $T_{pm}$ of the platelet pulses 52 and, also, by the coincidence-corrected red blood cell, or dominant, particle count R. More specifically, an accurate correction of the apparent platelet count $P_a$ has been determined to be readily achievable in accordance with the following equation 3:

$$P = \frac{P_a\left(1 + \frac{RT_{pm}}{IT}\right)}{\left(1 - \frac{DWT}{IT}\right)} \qquad 3$$

Figure 3:
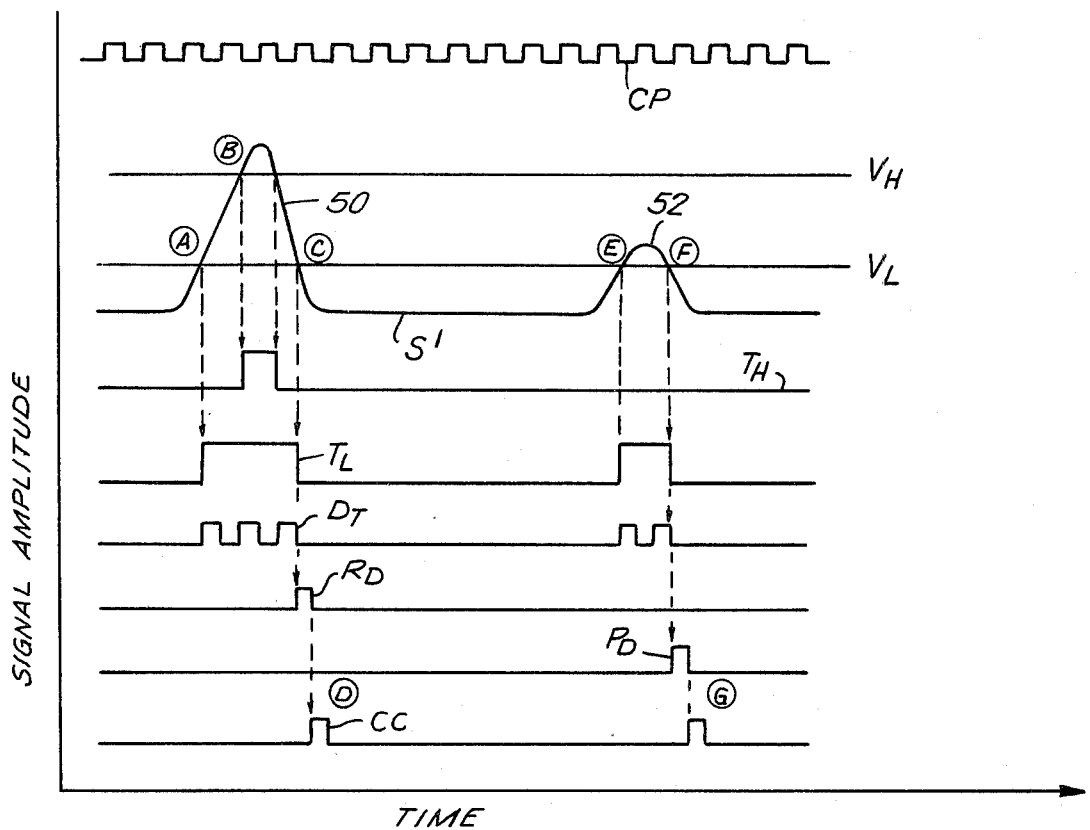
FIG. 3 is a series of waveforms, drawn to a same time scale, illustrating the operation of the counting circuit of FIG. 1.

Referring now to FIG. 3 for a detailed description of the particle counting circuit of FIG. 1, the waveform outputted from clock pulse source 22 is indicated at CP and the signal from detector 12 as amplified by amplifier 14 is indicated at S'. In respect of a red blood cell pulse 50, as the amplified signals S' goes above the low threshold detection level $V_L$ during the leading edge of the red cell pulse 50, indicated at A in FIG. 3, low threshold circuit 18 generates signal $T_L$ which is applied, as shown, to one input of AND gate 24. AND gate 24 is now enabled to pass clock pulses CP from clock pulse source 22, indicated by waveform $D_T$, to both counters 26 and 28. When S' goes above the high threshold level $V_H$, indicated at B in FIG. 3, high threshold circuit 16 generates signal $T_H$, which is applied to classification logic circuit 20, with the attendant classification of a red blood cell. When signal S' falls below the low threshold level $V_L$, illustrated at C in FIG. 3, the output signal $T_L$ of low threshold circuit 18 is terminated, so as to disable AND gate 24 and discontinue further counting of clock pulses CP by counters 26 and 28. Also, particle classification logic 20 generates a red blood cell decision pulse $R_D$ to increment counter 32, i.e., the red blood cell counter. At the termination of pulse $R_D$, particle classification logic 20 generates a counter clear pulse CC, indicated at D in FIG. 3, to clear counter 28.

In respect of a platelet pulse 52, as the signal S' again goes above the low threshold level $V_L$ during the leading edge of platelet pulse 52, indicated at E in FIG. 3, low threshold circuit 18 generates signal $T_L$ to again enable AND gate 24 to pass clock pulses CP from clock source 22 for counting by counters 26 and 28, again as indicated by waveform $D_T$. Thereafter, when the trailing edge of signal S' again crosses low threshold level $V_L$, indicated at F in FIG. 3, the output signal $T_L$ from low threshold circuit 18 is terminated to disable AND gate 24 and discontinue further counting of clock pulses CP by counters 26 and 28. At such time, a platelet decision pulse $P_D$ is generated by particle classification logic 20 and applied, as shown, to increment counter 30. In addition, the platelet decision pulse $P_D$ is applied, as shown, to latch 36, to cause the current value in such latch to be added by adder 34 to the count in counter 28, which added count is subsequently stored in latch 36. In addition, another counter clear pulse CC is generated by particle classification logic 20 to clear counter 28.

Thus is believed made clear that the particle classification logic circuit 20 functions to detect events defined by crossings of the low threshold level $V_L$. These events are subsequently identified as red cell events if, and only if, the high threshold level $V_H$ is also exceeded between those low threshold level crossings. Otherwise, the event is classified as a platelet event. At the end of the event in question, and in either case, a clear counter (CC) pulse is generated by circuit 20 to clear counter 28. Particle classification logic circuits of this operational configuration are known in the prior art as disclosed, for example at logic channels L1, L11, L111 and L1V of FIGS. 1B and 1C of U.S. Pat. No. 3,740,143 issued June 19, 1973 to Warren Groner, et al and assigned to the assignee hereof; and at the particle classification means structure of FIG. 12 of U.S. Pat. No. 3,502,974 issued Mar. 24, 1970 to W. H. Coulter, et al and assigned to Coulter Electronics, Inc. Regarding the logic channels L1, L11, L111 and L1V of U.S. Pat. No. 3,740,143, it may be seen that input pulses representative of the detection(s) of different types of leukocytes, or white blood cells, are differentiated through use in part of thresholding techniques and counted accordingly by appropriate gating of the resultant output signals to the including counters. Regarding the particle classification means structure of FIG. 12 of U.S. Pat. No. 3,502,974, it may be seen that input pulses representative of the detection(s) of different types of particles, for example different types of biological particles in the same suspension, are differentiated by threshold circuit 208 and low threshold circuit 204 and the resultant output signals counted accordingly by counter means 98 and 100. Mutual exclusivity of output signal counting is insured by inhibit means 212 which inhibit the incrementation of counter means 100 by an output signal from threshold circuit 204 in the event of a concomitant countable output signal from threshold circuit 208.

Operation of the circuit of FIG. 1 continues, as described, until red blood cell and platelet counting for the individual blood sample of interest is completed as set by system controller 42. During the time IT, the total of all counted platelet pulse widths $T_p$ (FIG. 2A) is stored in latch 36 as $TT_p$; the uncorrrected red blood cell count $R_a$ is stored in counter 32; the uncorrected platelet count $P_a$ being stored in counter 30; and the time DWT is stored in counter 26 in accordance with the number of clock pulses CP which have been counted. Equally clear, however, is the fact that not all of the platelets passed through the sheath-stream flow cell of particle counting apparatus 10 are included in count $P_a$. The fact that count $P_a$ does not reflect an accurate platelet count results, almost totally, from the red blood cell-platelet coincidence errors, of the type illustrated in FIG. 2B, inasmuch as the frequency of platelet-platelet coincidence is very small, so as to be of no consequence.

Under these circumstances, the times IT and DWT, respectively, are applied from system controller 42 and counter 26, respectively and as indicated in FIG. 1, to divider 46 and the value of the "dead time" term (DWT/IT) is decided. Such term (DWT/IT) is applied to the main logic circuit 43. Also, the uncorrected red blood cell count $R_a$ is applied, as indicated in FIG. 1, from counter 32 to main logic circuit 43, which accurately corrects red blood cell count R, in accordance with the known standard Equation 1.

Accurate, coincidence correction of the apparent platelet count $P_a$ in accordance with our invention is effected as follows: The apparent platelet count $P_a$ is applied, as indicated in FIG. 1, from counter 30 to main logic circuit 43 and divider circuit 38. The time-totalled pulse widths $TT_p$ of the counted platelets is applied from latch circuit 36 to divider circuit 38 and divided by $P_a$ to generate and apply the mean platelet pulse width $T_{pm}$ to multiplier 40. The corrected red blood cell count R is applied from computation logic 43 to multiplier 40, where it is multiplied by $T_{pm}$ to generate the term $RT_{pm}$ which is directed to divider 44. The interrogation time IT is applied, as indicated, from system controller 42 to divider 44 for division into $RT_{pm}$ to generate the term ($RT_{pm}$/IT), which is applied to the main logic circuit 43. Since the values of all of the terms of Equation 3 have now been provided to main logic circuit 43, the computation of the coincidence-corrected platelet count P is readily accomplished.

The system controller 42 which operates primarily to control the operation of the particle counting apparatus 10 and detector 12 to initiate and end each sample analysis period, and which thus does not, per se, form part of this invention, may for example take the conventional form of an appropriately configured microprocessor which, within the context of this invention, operates to clear counters 26, 28, 30 and 32 at the beginning of each sample analysis to initialize the same, and to measure the duration of each sample analysis period IT and apply that determination as shown in FIG. 1 to divider 46 thereby activating main logic circuit 43 to perform the described calculation functions. Main logic circuit 43 which may also, for example, take the form of an appropriately configured microproccessor, operates to record the values of $R_a$, $P_a$, (DWT/IT) and DWT as applied thereto as shown in FIG. 1 at the end of each sample analysis period, to calculate R in accordance with equation 1 hereinabove and output the same to multiplier 40 as shown in FIG. 1, and to calculate P in accordance with equation 3 hereinabove on the basis of the ($RT_{pm}$/IT) and (DWT/IT) terms as applied thereto from dividers 44 and 46, respectively, as shown in FIG. 1.

For use, as described hereinabove, with respect to an automated hematology system which operates upon each of a series of blood samples, in turn, it will be understood that the above-described operational and computational cycle would be completed once for each such sample.

Also, while described with respect to the correction of coincidence errors attendant the quantification of the red blood cells and platelets of blood samples, our invention is clearly not limited thereto, but rather, is applicable as well to correction of coincidence errors attendant the quantification of dominant and dominated particles, in any multi-particle systems, wherein the former have detectable characteristics which would render the otherwise detectable characteristics of the latter undetectable in a coincidence situation. These characteristics are by no means limited to particle shape, volume, size or ability to scatter or absorb or reflect light or other forms of energy, but, rather, may reside in, for example, different energy levels of high and low energy isotopes which are to be quantified in accordance with their respective energy levels. In such situations, the characteristics of the high energy isotopes would render the otherwise detectable characteristics of the low energy isotopes undetectable upon coincidence at the energy detecting means. Also, for applications wherein dominated particle-dominated particle coincidence errors are significant and must also be corrected to insure the accuracy of the dominated particle count, the standard coincidence errors correction Equation 2 may be utilized by the computation logic 43 to additionally correct the dominated particle count.

Various changes may, of course, be made in the described embodiment of the method and apparatus of our invention without departing from the spirit and scope thereof as defined by the appended claims.

What is claimed is:

1. In a method for the correction of coincidence errors which occur in the detecting and counting of mixed dominant and dominated particles wherein the detectable characteristics of the dominant particles are operable, under coincident dominant-dominated particle detection conditions, to render said dominated particles undetectable, the steps of, generating first signals corresponding to the detection of said dominant particles and counting said first signals corresponding to said dominant particles, generating second signals corresponding to the detection of said dominated particles and counting said second signals corresponding to said dominated particles, generating correction signals corresponding to the cumulative time duration for the detection of those of said dominated particles which are detected and counted, and correcting the count of said dominated particles in accordance with the cumulative time duration of said correction signals.

2. In a method as in claim 1 wherein, said correcting step further comprises, the step of, determining the mean time duration of said correction signals.

3. In a method as in claim 2 wherein, said correcting step further comprises, the steps of, multiplying the mean time duration of said correction signals by the count of said dominant particles, and dividing the resultant product by the total time for detecting said dominant and dominated particles to result in a quotient.

4. In a method as in claim 3 wherein, said correcting step further comprises, the step of, multiplying said quotient by the count of said dominated particles.

5. In a method as in claim 1 wherein, said correcting step is effected in accordance with the equation;

$$P = \frac{Pa\left(\dfrac{1 + RT_{pm}}{IT}\right)}{1 - \left(\dfrac{DWT}{IT}\right)}$$

wherein:
P is the coincidence-errors-corrected dominated particle count;
R is the coincidence-errors-corrected dominant particle count;
$T_{pm}$ is the mean duration in time of said correction signals;
$P_a$ is the dominated particle count;
IT is the total time of particle detection; and
DWT is the total time during which signals are being detected.

6. In apparatus for the correction of coincidence errors which occur in the detecting and counting of mixed dominant and dominated particles wherein the detectable characteristics of the dominant particles are operable, under coincident dominant-dominated particle detection conditions, to render said dominated particles undetectable, the improvements comprising, means to generate first signals corresponding to the detection of said dominant particles, means to count said first signals corresponding to said dominant particles, means to generate second signals corresponding to the detection of said dominated particles, means to count said second signals corresponding to said dominated particles, means to generate correction signals corresponding to the cumulative time duration for the detection of those of said dominated particles which are detected and counted, and means for correcting the count of said dominated particles in accordance with the cumulative time duration of said correction signals.

7. In apparatus as in claim 6 wherein, said means to correct said dominated particle count further comprise, means to determine the mean time duration of said correction signals.

8. In apparatus as in claim 7 wherein, said means to correct said dominated particle count further comprise, means to multiply said mean time duration by the count of said dominant particles to result in a product, and means to divide said product by the total dominant and dominated particle detecting time to result in a quotient.

9. In apparatus as in claim 8 wherein, said means to correct said dominated particle count further comprise, means to multiply said quotient by the count of said dominated particles.

* * * * *